United States Patent [19]

Flaugh

[11] Patent Number: 4,983,622

[45] Date of Patent: Jan. 8, 1991

[54] 6-SUBSTITUTED-4-DIALKYLAMINOTET-RAHYDROBENZ(C,D)INDOLES

[75] Inventor: Michael E. Flaugh, Indianapolis, Ind.

[73] Assignee: Eli Lilly and Company, Indianapolis, Ind.

[21] Appl. No.: 697,310

[22] Filed: Feb. 1, 1985

Related U.S. Application Data

[63] Continuation-in-part of Ser. No. 577,096, Feb. 6, 1984, abandoned.

[51] Int. Cl.$^5$ .................... A61K 31/40; C07D 209/90
[52] U.S. Cl. .................................. 514/411; 548/436
[58] Field of Search .................. 548/436; 424/274; 514/411

[56] References Cited

U.S. PATENT DOCUMENTS

| 3,200,130 | 8/1965 | Szmuszkovicz | 548/436 |
|---|---|---|---|
| 3,336,307 | 8/1967 | Shen | 548/436 |
| 4,110,339 | 8/1978 | Bach | 548/436 |
| 4,110,438 | 8/1978 | Bach et al. | 260/326.9 |
| 4,282,240 | 8/1981 | Baldwin | 548/436 |
| 4,576,959 | 3/1986 | Flaugh | 548/436 |
| 4,853,406 | 8/1989 | Rosentretter | 548/436 |

FOREIGN PATENT DOCUMENTS 0162695 11/1985 European Pat. Off. ............ 548/436
3346573 7/1985 Fed. Rep. of Germany .

OTHER PUBLICATIONS

Haefliger et al., Tetrahedron Letters, 25, 285 (1983).
Haefliger et al., ibid, 289.
Haefliger, H.C.A., 67, 1942 (1984).
Derwent Abstract No. 85-165,888/28 Abstracting EPO 148,440A.
Harris et al., J.P.E.T., 128, 358 (1960).
Kruse et al., J. Org. Chem., 49, 4761 (1984) (12/15/84 issue).
Mazurek et al., Chem. Abstr., vol. 102, entry 14280m (1985).

Primary Examiner—Donald G. Daus
Attorney, Agent, or Firm—Douglas J. Taylor; Leroy Whitaker; Bruce J. Barclay

[57] ABSTRACT (±)-4-substitutedamino-6-alkoxy, benzyloxy, acyloxy, or hydroxy-1,3,4,5-tetrahydrobenz[c,d]indoles, pharmaceutically acceptable salts thereof, are anti-depressants.

15 Claims, No Drawings

6-SUBSTITUTED-4-DIALKYLAMINOTETRAHYDROBENZ(C,D)INDOLES

CROSS-REFERENCE

This application is a continuation-in-part of my copending application Ser. No. 577,096 filed Feb. 6, 1984, now abandoned.

BACKGROUND OF THE INVENTION

The benz[c,d]indole ring system (I) has been known since 1949.

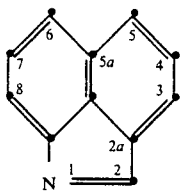

For example Uhle et al. *J. Am. Chem. Soc.*, 71, 1611 (1949); *ibid*, 73, 2402 (1951); Grob et al. *Helv. Chim. Acta.*, 33, 1796, 1955 (1950), 35, 2095 (1952), 36, 839 (1953) and Stoll et al. *ibid*, 33, 2254, 2257 (1950); 35, 148 (1952), prepared, among other compounds, a 5-keto-1,3,4,5-tetrahydrobenz[c,d]indole plus the corresponding 4-amino and 4-acetylamino derivatives. A useful starting material for the synthesis of these compounds was a 1-benzoyl-1,2,2a,3,4,5-hexahydro derivative, II.

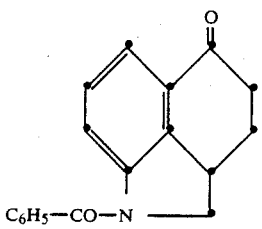

formed by the ring closure of 1-benzoyl-2(3-indolinyl)-propionylchloride under Friedel-Crafts conditions. Kornfeld et al., *J.A.C.S.*, 78, 3087 (1956) also prepared this compound and converted it, via a series of intermediates, to the 4-amino-5-keto derivative which was, in itself, a key intermediate in the first total synthesis of lysergic acid. In this synthetic procedure, a fourth ring (an N-methyl piperidine ring) was grafted onto an appropriately substituted tricyclic 1,2,2a,3,4,5-hexahydrobenz[c,d]indole. Stoll et al. *Helv. Chim. Acta*, 35, 148 (1952) also prepared (±)-4-dimethylamino-1,3,4,5-tetrahydrobenz[c,d]indole. Bach and Kornfeld, U.S. Pat. No. 4,110,339, prepared the corresponding 4-di-n-propylamino compound. Ledelec et al, U.S. Pat. No. 4,447,438 discloses 4-piperidyl-substituted-1H-indole having dopaminergic properties.

Certain naturally occurring alkaloids, agroclavine and elymoclavine, have been converted by Cassady et al. *J. Med. Chem.*, 17, 300 (1974) to N-methyldioxychanoclavine, N-methylchanoclavine, and chanoclavine, all 4,5-disubstituted tetrahydrobenz[c,d]indoles (III).

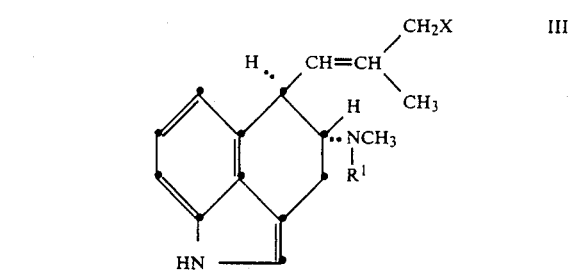

wherein X is H or OH and $R^1$ is $CH_3$ or H. Compounds according to III were without significant prolactin inhibiting activity, unlike the Bach-Kornfeld (±)-4-di-n-propylamino-1,3,4-5-tetrahydrobenz[c,d]indole, which was found to be a selective dopamine agonist as shown by its action in inhibiting dopamine uptake in vitro in bovine striatal membrane. The corresponding 4-(dimethyl)amino derivative of Stoll et al. (loc. cit.) was used only as an intermediate. The 4-aminotetrahydrobenz[c,d]indoles and related derivatives are weak serotonin antagonists with one exception, the 4-acetylamino-5-oxo derivative—see Harris and Uhle, *J. Pharm. & Exper. Therap.*, 128, 358 (1960).

SUMMARY OF THE INVENTION

This invention provides 4-aminosubstituted-6-substituted-1,3,4,5-tetrahydrobenz[c,d]indoles of the formula

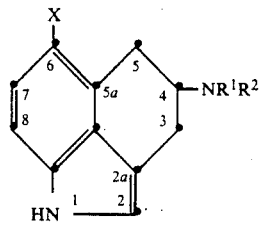

wherein $R^1$ and $R^2$ are individually hydrogen, methyl, ethyl, n-propyl or allyl, and X is an OH, $OC_{1-3}$ alkyl, O-benzyl, or O-acyl; and pharmaceutically acceptable salts thereof.

Illustrative of those groups which $NR^1R^2$ represents are included amino, methylamino, n-propylamino, ethyl-n-propylamino, diethylamino, ethylamino, n-propylamino and the like. The term "$C_{1-3}$ alkyl" as used herein includes the methyl, ethyl, n-propyl and isopropyl radicals. The term "acyl" includes groups derived from both carboxylic and sulfonic acids; i.e., groups of the general structure $R^3Z$ wherein Z is CO or $SO_2$ [indicating radicals derived from carboxylic (COOH) or sulfonic ($SO_2H$) acids] and $R^3$ is $C_{1-3}$ alkyl, $C_{3-8}$ cycloalkyl, phenyl, naphthyl and substituted phenyl wherein said substituents can be 1 or 2 members of the group halogen (Cl, Br, F), $C_{1-2}$ alkyl, $C_{1-2}$ alkyloxy or other biologically inert substituent. Illustrative acyl moieties include benzoyl, p-tosyl, acetyl, propionyl, isobutyryl, mesyl, ethylsulfonyl, n-propylsulfonyl, p-chlorobenzenesulfonyl, 3,4-methylenedioxybenzoyl, anisoyl, ethoxybenzenesulfonyl, 2,4-xylylsulfonyl, 3,4-dichlorobenzenesulfonyl, cyclopropylcarbonyl, cyclobutylsulfonyl, cycloheptylcarbonyl, cyclohexylcarbonyl, cyclooctylcarbonyl, cyclopentylcarbonyl, α-naphthoyl, β-naphthoyl, α-naphthylsulfonyl, β-naphthylsulfonyl, and the like groups. Since the O-acylated derivatives of IV above are chiefly useful as intermediates, or in some instances, as prodrugs, it will be apparent to those skilled in the art that other acyl groups than those enumerated above can function in an equivalent manner to protect the free OH group.

Compounds according to IV in which X is $O-C_{1-3}$ alkyl are, in addition, useful intermediates for preparing other compounds coming within the scope of this invention.

Pharmaceutically-acceptable acid addition salts of the compounds of this invention include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxyalkanoic and hydroxyalkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, naphthalene-1-sulfonate, naphthalene-2-sulfonate, mesylate and the like salts.

The compounds of formula IV are central serotonin agonists, useful as anti-depressants. Thus, included within the present invention is a pharmaceutical formulation which comprises as an active ingredient a compound of formula IV, or a pharmaceutically-acceptable salt thereof, associated with one or more pharmaceutically-acceptable carriers or excipients therefor. The formulation, or the active ingredient thereof, can be used as a method of treating depression, obesity, alcoholism, smoking, or senile dementia in a warm-blooded animal by administering to said animal a therapeutically-effective amount of a compound of formula IV, or a pharmaceutically-acceptable acid addition salt thereof.

Compounds according to formula IV have an asymmetric center at C-4 and thus occur as a (±)- or dl racemic mixture. This invention includes both stereoisomers represented by formula IV. The individual stereoisomers can be prepared by resolving a racemate of a 2,2a-dihydro indole intermediate (XIV, XIVa, XV, XVa, XVI, XVIa from Reaction Scheme 1), and then oxidizing the separated stereoisomer to the indole (XVII and XVIIa). Further reactions can then be carried out if needed to obtain a desired optically active product of formula IV. The resolution procedure can employ optically-active acids such as, for example, L-(+)-R-tartaric acid, (−)-dibenzoyltartaric acid, (+)-camphoric acid, (+)-10-camphorsulfonic acid, (−)-mandelic acid, (−)-malic acid, N-acetyl-L-glutamic acid, t-BOC-D-phenylglycine, D-(−)-S-tartaric acid, L-p-toluoyl-tartaric acid and the like.

Compounds illustrative of the scope of this invention include:

(±)-4-diallylamino-6-ethoxy-1,3,4,5-tetrahydrobenz[c,d]indole sulfate (±)-4-methylethylamino-6-hydroxy-1,3,4,5-tetrahydrobenz[c,d]indole tartrate (+)-4-dimethylamino-6-methoxy-1,3,4,5-tetrahydrobenz[c,d]indole maleate (±)-4-diallylamino-6-methoxy-1,3,4,5-tetrahydrobenz[c,d]indole succinate (±)-4-diethylamino-6-methoxy-1,3,4,5-tetrahydrobenz[c,d]indole phosphate (−)-4-methyl-n-propylamino-6-n-propoxy1,3,4,5-tetrahydrobenz[c,d]indole dihydrogenphosphate (±)-4-(di-n-propyl)amino-6-acetoxy-1,3,4,5-tetrahydrobenz[c,d]indole bisulfate (±)-4-dimethylamino-6-propionoxy-1,3,4,5-tetrahydrobenz[c,d]indole hydrobromide (±)-4-diethylamino-6-benzyloxy-1,3,4,5-tetrahydrobenz[c,d]indole tosylate (−)-4-diallylamino-6-hydroxy-1,3,4,5-tetrahydrobenz[c,d]indole malate (±)-4-(di-n-propyl)amino-6-hydroxy-1,3,4,5-tetrahydrobenz[c,d]indole benzoate (−)-4-diethylamino-6-benzyloxy-1,3,4,5-tetrahydrobenz[c,d]indole phenylacetate (+)-4-dimethylamino-6-mesyloxy-1,3,4,5-tetrahydrobenz[c,d]indole 1,4-butyndioate (±)-4-diallylamino-6-p-tosyloxy-1,3,4,5-tetrahydrobenz[c,d]indole hydrochloride (±)-4-dimethylamino-6-p-toluyl-1,3,4,5-tetrahydrobenz[c,d]indole sulfate (+)-4-(di-n-propyl)amino-6-hydroxy-1,3,4,5-tetrahydrobenz[c,d]indole fumarate (−)-4-amino-6-hydroxy-1,3,4,5-tetrahydrobenz[c,d]indole propiolate and the like.

Compounds according to IV above wherein X is $O-C_{1-3}$ alkyl are prepared according to the following reaction scheme.

Reaction Scheme 1
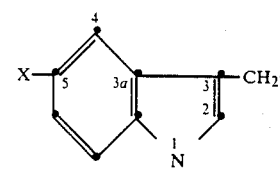
V
1. NaCNBH₃
   HOAc
2. C₆H₅COCl
   pyridine
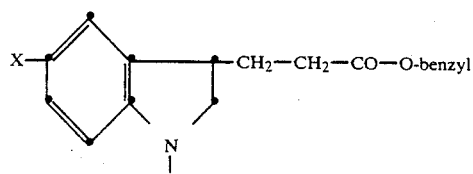
VI
3. H₂, Pd-on-C
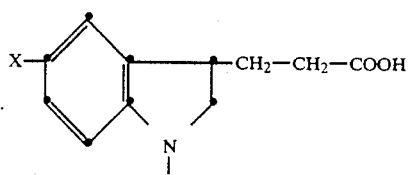
VII
4. PPA
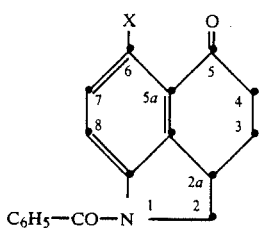
VIII
5. NaBH₄
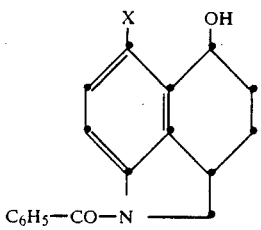
IX
H⁺
Heat -continued
Reaction Scheme 1
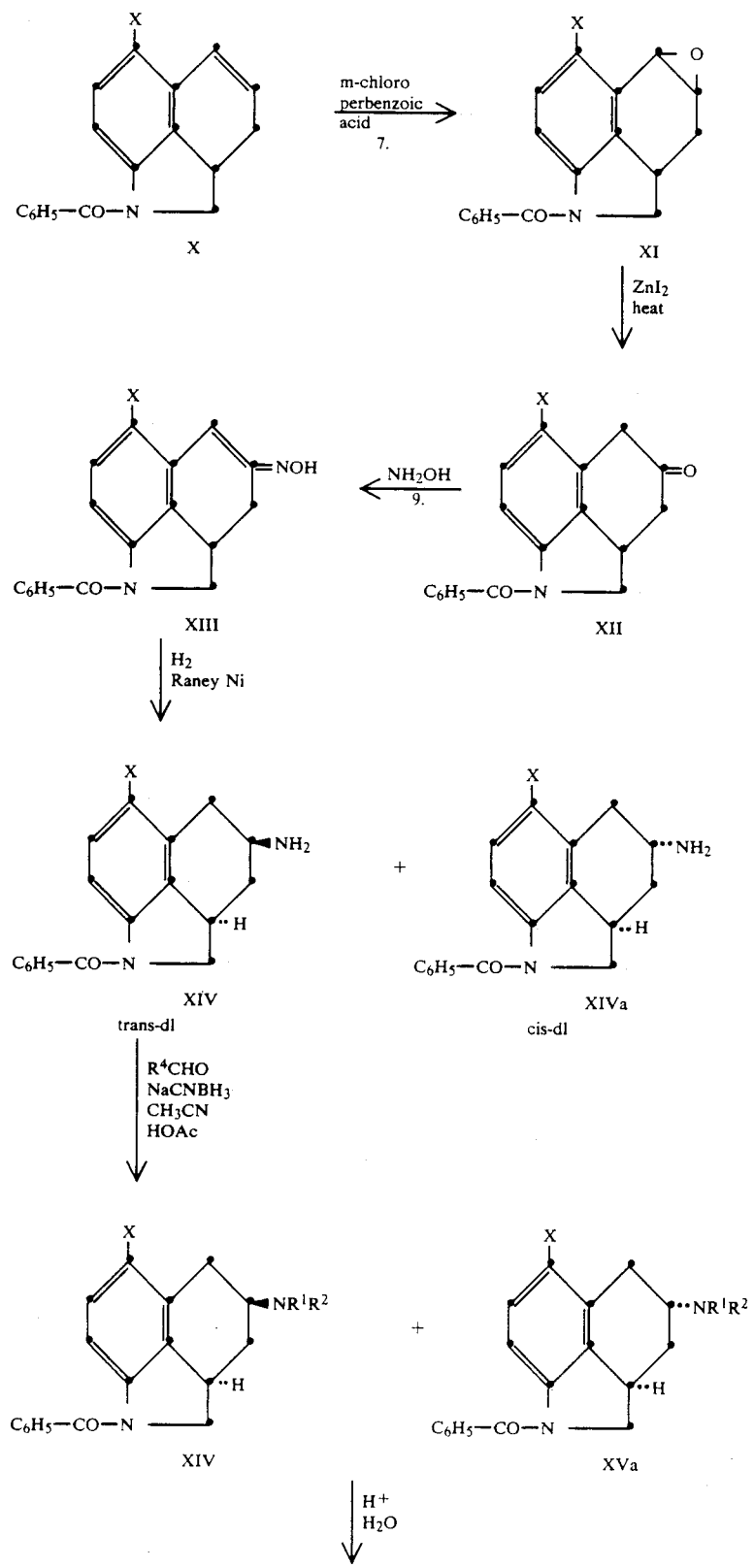

Reaction Scheme 1

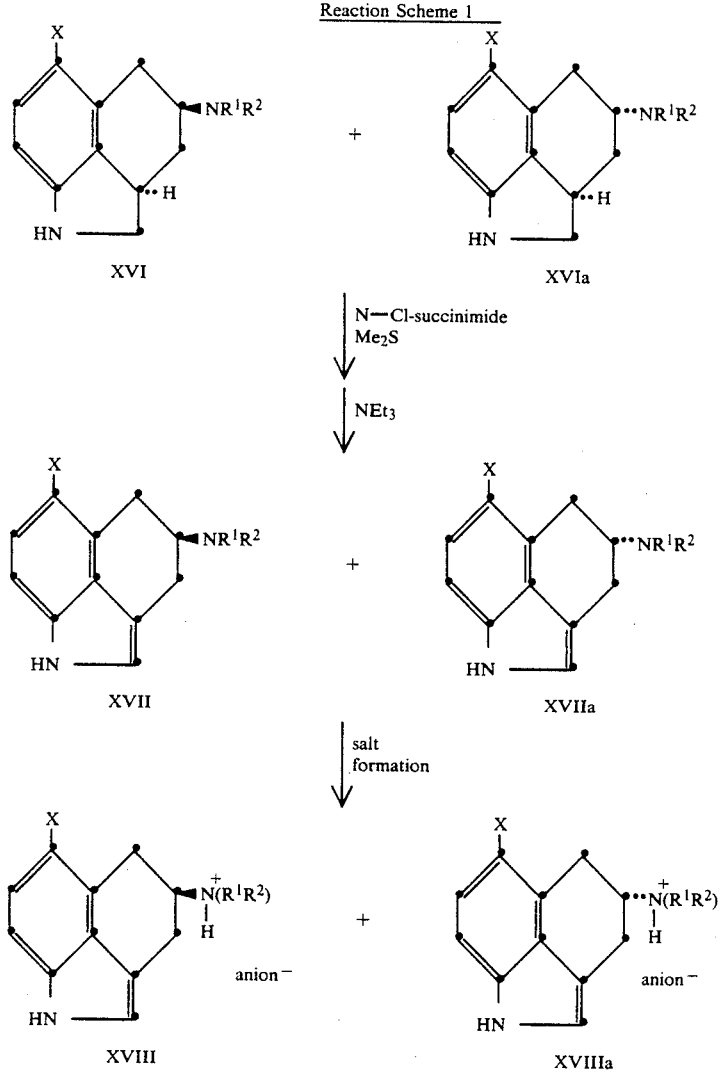

wherein $R^4$ is H, $CH_3$ or $C_2H_5$, X is $O-C_{1-3}$ alkyl or O-benzyl and $R^1$ and $R^2$ have their previous meanings.

According to Reaction Scheme 1, where X is methoxy, $R^4$ is ethyl and $R^1$ and $R^2$ are n-propyl for the sake of convenience only, a benzyl 3-(5-methoxy-3-indolyl)propionate or the like ester (V) is reduced with (1) sodium cyanoborohydride to the corresponding 2,3-dihydro compound. (The Arabic numerals in Reaction Scheme 1 in parentheses refer to reagents used). With the saturation of the 2,3 double bond, the 1-amino group loses much of its acidic character and becomes sufficiently basic to enable it to be protected with a standard amine protecting group such as an acyl group; i.e., as a benzoyl derivative. This protective group is formed by reacting the 2,3-dihydro compound with (2) an acyl halide or anhydride; for example, benzoyl chloride in the presence of pyridine, to yield VI. The free acid (VII) is then prepared from the benzoyl ester (VI) by hydrogenation (3) over a noble metal catalyst in a mutual inert solvent. The noble metal catalyst of choice is palladium-on-carbon. The free acid thus produced—3-(5-methoxy-1-benzoyl-2,3-dihydro-3-indolyl)propionic acid—is cyclized with a dehydrating agent, preferably polyphosphoric acid (PPA) (4). This reagent is a particularly convenient cyclizing agent since it can also serve as a solvent for the cyclization reaction. Alternatively, the acid chloride can be prepared and cyclized in the presence of a Lewis acid, preferably $AlCl_3$—see Kornfeld et al., J.A.C.S., 78, 3087 (1956)—to yield the desired benz[c,d]indole. The cyclized product (VIII) is 1-benzoyl-5-oxo-6-methoxy-1,2,2a,3,4,5hexahydrobenz[c,d]indole. Reduction (5) of the oxo group with sodium borohydride in a lower alkanol such as ethanol yields the corresponding 5-hydroxy derivative (IX). This hydroxy derivative can be dehydrated by heating in the presence of an acidic catalyst (p-toluene sulfonic acid (6) for example) in an inert solvent to yield 1-benzoyl6-methoxy-1,2,2a,3-tetrahydrobenz[c,d]indole (X). I prefer, however, to use an acidic ion exchange resin as the acid catalyst. The 4,5 double bond is then epoxidized with a reagent such as m-chloroperbenzoic acid (7) in an inert solvent to yield a 4,5-epoxy derivative (XI). Rearrangement of the epoxide by heating in the presence of zinc iodide (8) yields an isomeric ketone, (isomeric with VIII), 1-benzoyl-4-oxo-6-methoxy-1,2,2a,3,4,5-hexahydrobenz[c,d]indole (XII).

Next, the hydroxylamine derivative of this isomeric ketone (XIII) is formed (9) and the resulting oxime reduced with Raney nickel (10) to yield a mixture of amino derivatives, trans-dl and cis-dl-1-benzoyl-4-amino-6-methoxy-1,2,2a,3,4,5-hexahydrobenz[c,d]indole (XIV and XIVa). Alkylation (11) of the primary amine group by standard procedures, for example reductive alkylation with an aldehyde, R⁴CHO, and sodium cyanoborohydride in acetonitrile, to which an equivalent of glacial acetic acid has been added, yields the symmetrical di-alkylamine; (XV and XVa). Treatment of the mixture of these cis-dl and trans-dl tertiary amines with aqueous acid (12) yields a mixture comprising trans-dl-4-dialkylamino-6-methoxy-1,2,2a,3,4,5-hexahydrobenz[c,d]indole and the corresponding cis-dl compound. Oxidation of this mixture with, for example, N-chloro succinimide (13) in the presence of dimethyl sulfide and triethylamine (14), yields (±)-4-dialkylamino-6-methoxy-1,3,4,5-tetrahydrobenz[c,d]indole (XVII and XVIIa represent the two enantiomers). The racemic mixture can readily be converted to the salt form (XVIII and XVIIIa) by standard procedures (15).

While the above procedure has been illustrated with reference to the preparation of a 6-methoxy derivative, the procedure is equally applicable to the preparation of other 6-C$_{1-3}$ alkyloxy compounds or of 6-benzyloxy compounds or the 6-fluoro compound.

The procedure represented in Reaction Scheme 1 is particularly useful for preparing compounds according to IV in which the 6-derivative (X group) is alkyloxy. These 6-alkyloxy compounds can be prepared by an alternate procedure. According to this procedure, the intermediate disclosed by Bach and Kornfeld in U.S. Pat. No. 4,110,339, Example 1; to wit, 1-benzoyl4-(di-n-propyl)amino-1,2,2a,3,4,5-hexahydrobenz[c,d]indole or the corresponding 4-dimethylamino, 4-diethylamino or mixed N,N-dialkyl derivative, is brominated by standard procedures at C-6. The 6-bromo compound thus formed, can be treated with sodium methoxide in the presence of CuI to yield a 6-methoxy derivative. The benzoyl protecting group is then removed from the indole nitrogen by treatment with aqueous acid. As in the procedure in Reaction Scheme 1, as a final step, the 6-alkoxy substituted-4-dialkylamino-1,2,2a,3,4,5-hexahydrobenz[c,d]indole is oxidized to reconstitute the indole ring and yield a compound according to IV above wherein X is alkyloxy. The 6-benzyloxy derivatives are prepared in similar fashion.

I have developed a process for preparing (±)-4-dialkylamino-6-bromo-1,2,2a,3,4,5-hexahydrobenz[c,d]indole which commences with brominating the Bach-Kornfeld (loc.cit.) cyclic ketone. This process is set forth in Reaction Scheme 2 below, using the preparation of a 4-di-n-propyl derivative for illustrative purposes only.

Reaction Scheme 2

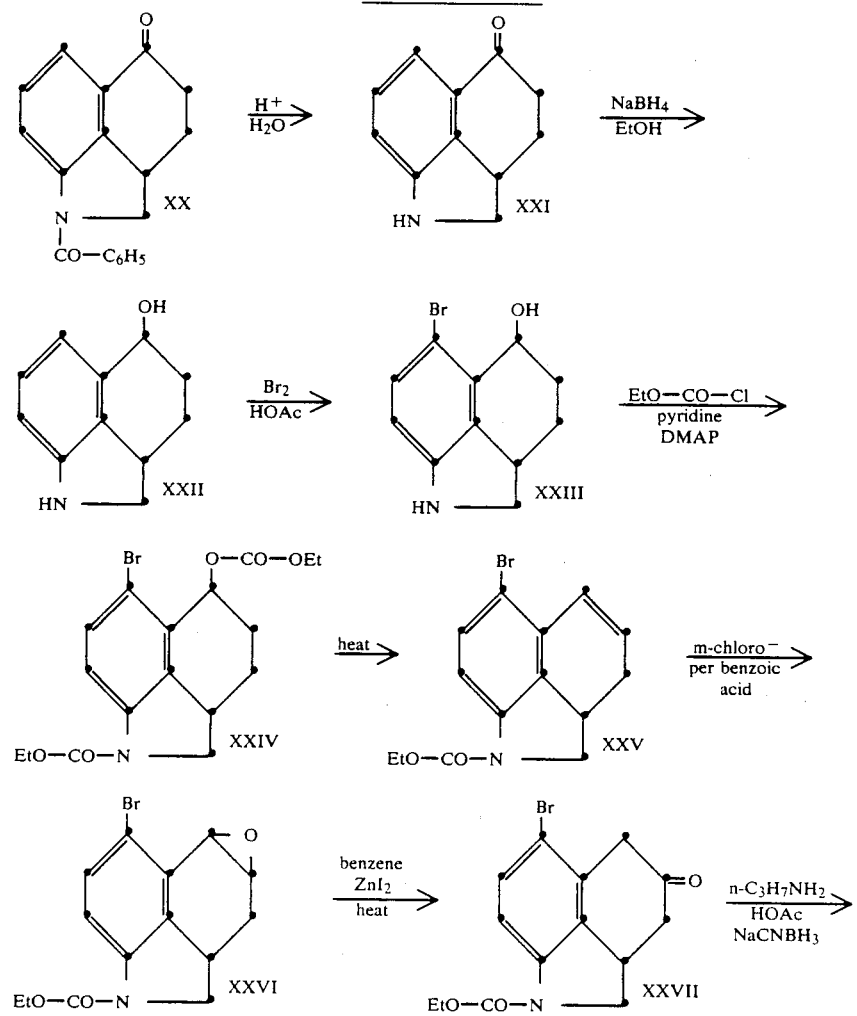

Reaction Scheme 2

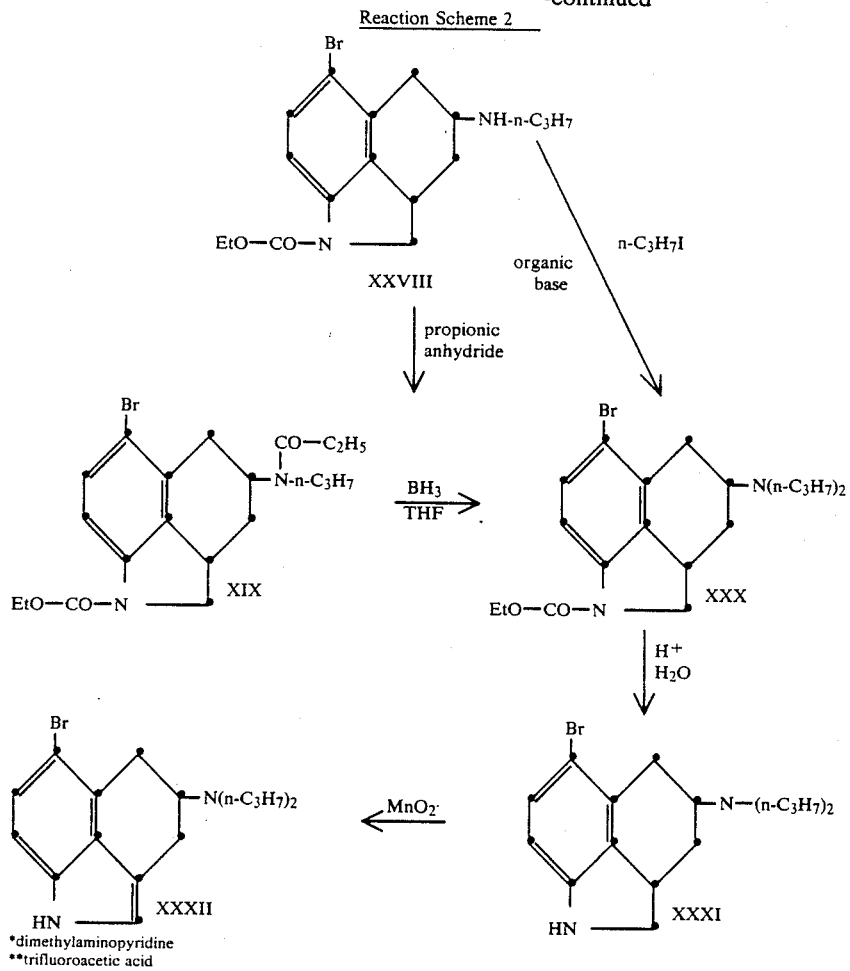

*dimethylaminopyridine
**trifluoroacetic acid

Specifically, 1-benzoyl-5-oxo-1,2,2a,3,4,5hexahydrobenz[c,d]indole (XX) (from Kornfeld et al, *J.A.C.S.*, 78, 3887 (1956) compound 4) is hydrolysed in acid to 5-oxo-1,2,2a,3,4,5-hexahydrobenz[c,d]indole (XXI) (compound 10 of Kornfeld et al when R is H). The 5-ketone is reduced to a 5-hydroxyl[(±)-5-hydroxy-1,2,2a,3,4,5-hexahydrobenz[c,d]indole (XXII)] with an alkali metal borohydride or alumina hydride in a mutual inert solvent. Bromination in acetic acid yields the (±)-6-bromo-5-hydroxy derivative (XXIII). This compound is then reacted with 2 moles of ethyl chloroformate to yield a (±)-1-ethoxycarbonyl-5-ethoxycarbonyloxy-6-bromo-1,2,2a,3,4,5-hexahydrobenz[c,d]indole (XXIV). This double acylation is conveniently carried out in pyridine solution (though other inert solvents may be used) containing the optional catalyst DMAP. Heating the 5-ethoxy carbonyloxy compound results in elimination to produce 1-ethoxycarbonyl-6-bromo-1,2,2a,3-tetrahydrobenz[c,d]indole (XXV). Epoxidation of the thus-produced double bond using, conveniently, m-chloroperbenzoic acid or other peracid as in Reaction Scheme 1 with the corresponding 1-benzoyl derivative (X→XI). Rearrangement of the epoxide on heating with $ZnI_2$ yields the 4-oxo derivative (XXVII). Here again, the reaction conditions from Reaction Scheme 1 (XI→XII) can be employed. Reductive amination with n-propyl bromide and $NaCNBH_3$ or other suitable reducing agent, yields (±)-1-ethoxycarbonyl-4-n-propylamino-6-bromo-1,2,2a,3,4,5-hexahydrobenz[c,d]indole (XVIII). This secondary amine can then be acylated with propionic anhydride and the N-propionyl group reduced with $BH_3$ in TFA or $NaCNBH_3$ or other suitable reducing agent to yield the 4-di-n-propyl compound, (±)-1-ethoxycarbonyl-4-di-n-propylamino 6-bromo-1,2,2a,3,4,5-hexahydrobenz[c,d]indole (XXXI). Alternative, the secondary amine XXVIII can be acylated as with n-propyliodide in the presence of an organic base to yield XXXI directly. Finally, hydrolysis of the 1-ethoxycarbonyl amide yields XXXI, oxidation of which with $MnO_2$ or with N-chlorosuccinimide in the presence of dimethyl sulfide yields a 2,2a-didehydro derivative (XXXII). An inert solvent is employed. In general, the reaction conditions from Reaction Scheme 1 are operative here. (XVI+XVIa to XVII+XVIIa). The ultimate product of this reaction (XXXII) is the desired intermediate (±)-4-di-n-propylamino-6-bromo-1,3,4,5-tetrahydrobenz[c,d]indole.

The above reaction sequence has been illustrated with respect to the preparation of a 4-di-n-propyl derivative. It will be apparent to those skilled in the art that substitution of methyl, ethyl or allyl amine for n-propylamine in the preparation of XXVIII would yield a 4-methyl, ethyl or allyl amino group. Likewise the thus formed secondary amine can be acylated (XXVIII where the amine group is n-propyl but could be Me, Et or allyl) with formic, acetic, acrylic or propionic acid and the resulting N-acyl group reduced to an alkyl or allyl group to form a compound of the formula

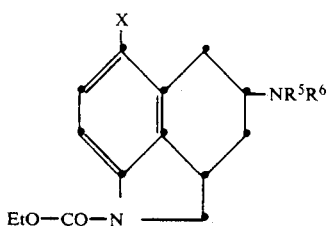

XXXa wherein X is O-C$_{1-3}$ alkyl, and R$^5$ and R$^6$ are, individually, methyl, ethyl, n-propyl or allyl. It will be noted that the above procedure provides an easy route to unsymmetrically substituted C-4 tertiary amines.

Alternatively, the secondary amine (XXVIII where the amine group is n-propyl but could be methyl, ethyl or allyl) can be directly alkylated with CH$_3$I, C$_2$H$_5$I, n-propyl iodide or allyl bromide to yield the same tertiary amine (XXXa).

Compounds according to IV in which X is hydroxy are prepared by debenzylation of the corresponding derivative in which X is benzyloxy. Alternatively, the 6-bromo group in a (±)-4-dialkyl (or allyl)amino-6-bromo-1,3,4,5-tetrahydrobenz[c,d] indole, can be replaced by a benzyloxy group. Debenzylation by hydrogenation in neutral or slightly acidic solution is a convenient way to prepare the 6-hydroxy derivative, although the yield is poor. The 6-hydroxy derivatives are relatively unstable, and it is prudent to protect a compound containing this group from oxidation by acylation, as with acetic anhydride, or by immediate conversion to a salt. The 6-acyloxy derivatives thus formed can act as prodrugs in that, after administration, the acyloxy group will be hydrolyzed to yield the free 6-hydroxy compound in vivo.

Compounds according to IV above have a single asymmetric center at C-4 and occur commonly as a racemate. However, as has been pointed out in the above discussion of Reaction Scheme 1, compounds according to VIII through XVI and XVIa have an additional asymmetric center at C-2a, which center is removed by the oxidative procedures (13) and (14). Thus, compounds IX, XIV, XIVa, XV, XVa, XVI and XVIa each have two asymmetric centers (at C-2a and C-4) and exist as two racemic pairs conveniently designated as the trans-dl and the cis-dl racemates.

This invention is further illustrated by the following specific examples.

EXAMPLE 1

Preparation of (±)-4-di-n-propylamino-6-methoxy-1,3,4,5-tetrahydrobenz[c,d]indole A solution was prepared by dissolving 26 g. of benzyl 2-(5-methoxy-3-indolyl)propionate in 500 ml. of glacial acetic acid. The solution was cooled and stirred. Twenty-six grams of sodium cyanoborohydride were added. The resulting reaction mixture was stirred at ambient temperature for about 3.5 hours at which time TLC showed no peak corresponding to starting material, indicating the reaction had gone substantially to completion. The reaction mixture was then poured into 2 l. of water and the aqueous mixture extracted with several portions of methylene dichloride. The methylene dichloride extracts were combined, the combined extracts washed with dilute aqueous sodium bicarbonate and then dried. Removal of the solvent in vacuo yielded 25.5 g. of a viscous oil comprising benzyl 2-(5-methoxy-3-indolinyl)propionate formed in the above reaction. The oil was dissolved in chloroform and 8 ml. of pyridine were added to the chloroform solution. Next, 13.9 g. of benzoylchloride were added while the solution was being cooled in an ice-water bath. After the addition had been completed, the acylation mixture was stirred for about one hour and was then washed once with water, twice with 1N aqueous hydrochloric acid, twice with dilute aqueous sodium bicarbonate and finally with saturated aqueous sodium chloride. The aqueous washes were all discarded. The organic layer was dried and the solvent removed in vacuo. The resulting residue was dissolved in ethyl acetate and the ethyl acetate solution passed over a short Florisil column. Ethyl acetate was removed from the eluate. Benzyl 2-(1-benzoyl-5-methoxy-3-indolinyl)propionate thus prepared crystallized on standing overnight. The crystals were washed with cyclohexane. Recrystallization from a toluene-hexane solvent mixture yielded 30.2 g. of benzyl 2-(1-benzoyl-5-methoxy-3-indolinyl)propionate melting at about 102°-3° C.

The compound had the following physical properties:

Ultraviolet spectrum; $\lambda_{max}$ (MeOH) 274 nm ($\epsilon$=11,900); NMR (CDCl$_3$) $\delta$=2.0 (mult, 2H, $\alpha$—CH$_2$), 2.4 (mult, 2H, $\beta$-CH$_2$), 3.3 (mult, 1H, 3—H), 3.7 (mult, 1H, 2$\beta$—H), 3.8 (s, 3H, OCH$_3$), 4.2 (qt, 1H, 2$\beta$—H), 5.1 (s, 2H, PhCH$_2$), 6.7 (mult, 1H, 7—H), 6.9 (brs, 1H, 4—H), 7.3 (mult, 1H, 8—H), 7.4 (s, 5H, Ph), 7.5 (s, 5H, Ph—CO).

Analysis Calculated: C, 75.16; H, 6.07; N, 3.37;
Found: C, 74.96; H, 5.88; N, 3.19.

Thirty grams of benzyl 2-(1-benzoyl-5-methoxy-3-indolinyl)propionate were hydrogenated over palladium-on-carbon in ethanol to remove the benzyl ester group. 2-(1-Benzoyl-5-methoxy-3-indolinyl)propionic acid thus formed crystallized on cooling in the hydrogenation bomb and separated with the catalyst on filtration. The desired product was dissolved away from the catalyst by washing with hot ethanol. Ethanol was removed from the combined filtrate and washings by evaporation. The resulting residue was dissolved in tetrahydrofuran (THF). The THF solution was filtered and the THF removed from the filtrate in vacuo. The resulting residue was crystallized from about 500 ml. of ethanol; yield=21.2 g. of 2-(1-benzoyl-5-methoxy-3-indolinyl)propionic acid melting at 169°-70° C.

Ultraviolet spectrum: $\lambda_{max}$ (MeOH) 274 nm ($\epsilon$=12,200)

Analysis Calculated: C, 70.14; H, 5.89; N, 4.31
Found: C, 70.42; H, 5.99; N, 4.62

A repeat hydrogenation on 17 g. of ester starting material in 125 ml. of THF and 125 ml. of ethanol using 0.5 g. of 10% Pd/C and a hydrogen pressure of 2.74×10$^6$ dynes/cm$^2$ gave a 94% yield of the desired acid.

Five grams of 2-(1-benzoyl-5-methoxy-3-indolinyl)-propionic acid were cyclized in 100 g. of polyphosphoric acid (PPA) at 80° C. TLC after one hour of reaction time indicated little or no starting material present. The reaction mixture was therefore poured over ice. The resulting aqueous mixture was extracted several times with methylene dichloride. The methylene dichloride extracts were combined and the combined extracts washed with sodium bicarbonate until the washings remained basic to litmus. The extracts were then concentrated in vacuo and the resulting residue recrystallized from a toluene/hexane solvent mixture to yield crystalline 1-benzoyl-5-oxo-6-methoxy-1,2,2a,3,4,5-hexahydrobenz[c,d]indole formed in the above cyclization. Recrystallization yielded about 4.5 g. of compound melting at about 147.5°-149° C.

The compound had the following physical characteristics:

Infrared spectrum (KBr): 1634, 1672 cm$^{-1}$ NMR (DMSO-d$_6$) $\delta$=1.81 (quintet, 1H, 3$\beta$—H), 2.18 (brd, 1H, 3$\alpha$—H), 2.53 (mult, 2H, 4—CH$_2$), 3.33 (mult, 1H, 2$\beta$—H), 3.61 (mult, 1H, 2a—H), 3.80 (s, 3H, OCH$_3$), 4.14 (mult, 1H, 2$\alpha$—H), 6.97 (mult, 1H, 7—H), 7.59 (mult, 5H, Ph), 8.11 (mult, 1H, 8—H).

Analysis Calculated: C, 74.25; H, 5.58; N, 4.56;
Found: C, 73.99; H, 5.84; N, 4.37.

A second large-scale run using 18.95 g. of free acid starting material gave a crude product which, when combined with the product from the first reaction, yielded, after recrystallization, 29.9 g. (84% yield) of cyclized product melting at about 152°-3° C.

A suspension of 4.2 g. of 1-benzoyl-5-oxo-6-methoxy-1,2,2a,3,4,5-hexahydrobenz[c,d]indole in 50 ml. of ethanol was prepared. A solution of 0.77 g. of sodium borohydride in 25 ml. of ethanol was added thereto in dropwise fashion with stirring. The suspended ketone slowly dissolved to produce a greenish solution. After about four hours of stirring at room temperature, the now homogeneous reaction mixture was concentrated in vacuo. Fifty ml. of water were added to the residue and the resulting basic aqueous solution neutralized with 3N aqueous hydrochloric acid to pH=7. This neutral aqueous layer was extracted several times with methylene dichloride. The methylene dichloride extracts were combined and the combined extracts washed with saturated aqueous sodium chloride and then dried. Removal of the solvent by evaporation left a viscous oil. Chromatography of this oil over silica gel using ethyl acetate as the eluant yielded 3.83 g. (90% yield) of ($\pm$)-1-benzoyl-5-hydroxy-6-methoxy-1,2,2a,3,4,5hexahydrobenz[c,d]indole. Recrystallization from ethyl acetate of a 100 mg. sample of the crystalline product gave 68 mg. of the mixture of epimeric alcohols.

Infrared spectrum (CHCl$_3$): 1632 cm$^{-1}$;
Ultraviolet spectrum: $\lambda_{max}$ (MeOH) 273 nm ($\epsilon$=7900), 302
nm (sh) ($\epsilon$=6000)
Analysis Calculated: C, 73.77; H, 6.19; N, 4.53;
Found: C, 73.71; H, 6.03; N, 4.43.

A reaction mixture was prepared from 3.7 g. of ($\pm$)-1-benzoyl-5-hydroxy-6-methoxy-1,2,2a,3,4,5-hexahydrobenz[c,d]indole, 1 g. of a macroreticular dehydration catalyst (AMBERLYST-15 resin) and 50 ml. of toluene. The reaction mixture was heated to reflux for about one hour in an apparatus equipped with a Dean-Stark trap. The amount of water collected in the trap plus TLC on the reaction mixture indicated that dehydration was complete at this time. ($\pm$)-1-Benzoyl-6-methoxy-1,2,2a,3-tetrahydrobenz[c,d]indole was formed in the above dehydration. The reaction mixture was filtered through filter cell. Evaporation of the filtrate to dryness yielded a viscous oil, which crystallized on trituration with hexane to give 3.34 g. of ($\pm$)-1-benzoyl-6-methoxy-1,2,2a,3-tetrahydrobenz[c,d]indole (96% yield). Recrystallization of a 100 mg. sample from a toluene/hexane solvent mixture yielded 85 mg. of compound melting at about 125.5°-127° C.

Ultraviolet spectrum: $\alpha_{max}$ (MeOH) 271 nm ($\alpha$=13,300), 320 nm (sh) ($\epsilon$=3500).
Analysis Calculated: C, 78.33; H, 5.88; N, 4.81;
Found: C, 78.09; H, 5.68; N, 4.65.

A solution of 3.2 g. of ($\pm$)-1-benzoyl-6-methoxy-1,2,2a,3-tetrahydrobenz[c,d]indole in 120 ml. of chloroform was cooled to about 0° C. with stirring. Three and sixty-one hundredths grams of 80-85% m-chloroperbenzoic acid were added thereto. The resulting solution was stirred in the 0°-5° C. range for about five hours after which time TLC showed no remaining starting material. The reaction mixture was then washed twice with cold 1N aqueous sodium hydroxide, twice with dilute aqueous sodium bisulfite and again with 1N aqueous sodium hydroxide. The washings were discarded. The remaining organic layer was then dried and the solvent removed in vacuo. The residual oil crystallized to yield 1-benzoyl-4,5-epoxy-6-methoxy-1,2,2a,3,4,5-hexahydrobenz[c,d]indole. The compound melted at 174°-175° C. after recrystallization from toluene.

Ultraviolet spectrum: $\lambda_{max}$ (MeOH) 273 nm ($\epsilon$=10,700), 300 nm (sh) ($\epsilon$=7700).
Analysis Calculated: C, 74.25; H, 5.58; N, 4.51;
Found: C, 73.98; H, 5.70; N, 4.37.

A solution of the epoxidized product in benzene solution was, without further purification, added to a suspension of 1.8 g. of zinc iodide in 150 ml. of benzene. (The suspension was dried by distillation of about 30 ml. of benzene containing some benzene-water azeotrope.) The addition was made in dropwise fashion over a ten minute period at a temperature of about 50° C. The reaction mixture was heated to refluxing temperature for about 50 minutes and was then cooled. The cooled reaction mixture was washed with dilute aqueous hydrochloric acid in order to decompose any reaction complex present. The organic solution was next washed with saturated aqueous sodium bicarbonate. The solvent was removed from the organic layer in vacuo and the resulting residue was recrystallized from ethyl acetate. ($\pm$)-1-Benzoyl-4-oxo-6-methoxy-1,2,2a,3,-4,5-hexahydrobenz[c,d]indole thus prepared melted at about 188°-189° C. after two recrystallizations (yield=72%).

The compound had the following physical characteristics:

Infrared spectrum (CHCl$_3$): 1636, 1717 cm$^{-1}$; NMR (CDCl$_3$) $\delta$=2.34 (qt, 1H, 3$\beta$—H), 2.90 (brd, 1H, 3$\alpha$—H), 3.31 (d, 1H, 5$\beta$—H), 3.66 (d, 1H, 5$\alpha$—H), 3.8 (mult, 2H, 2a—H and 2$\beta$—H), 3.80 (s, 3H, OCH$_3$), 4.33 (mult, 1H, 2$\alpha$—H), 6.75 (mult, 1H, 7—H), 7.54 (mult, 5H, Ph), 7.96 (mult, 1H, 8—H).

Analysis Calculated: C, 74.23; H, 5.58; N, 4.56;
Found: C, 74.24; H, 5.37; N, 4.50.

A reaction mixture was prepared from 207 mg. of ($\pm$)-1-benzoyl-4-oxo-6-methoxy-1,2,2,3,4,5-hexahydrobenz-[c,d]indole and 200 mg. of hydroxylamine hydrochloride in 5 ml. of ethanol plus 1 ml. of pyridine. The reaction mixture was heated to reflux temperature for about 15 minutes and then was cooled. An equal volume of water was added. At this point, the oxime formed in the above reaction began to crystallize. Crystallization was allowed to proceed to completion. The reaction mixture was filtered. Additional water added to the filtrate produced a second crop of crystals; total yield=0.21 g. (98% total yield). The crystalline product, a mixture of syn and anti-($\pm$)-1-benzoyl-4-oximino-6-methoxy-1,2,2a,3,4,5-hexahydrobenz[c d]indole formed in the above reaction, melted at about 189°-190°

C. Recrystallization yielded material melting at about 193° C.

Mass spectrum: 322 (mass peak).

Analysis Calculated: C, 70.79; H, 5.63; N, 8.69;

Found: C, 70.86; N, 5.47; N, 8.46.

A mixture of syn and anti-oximes (2.46 g.) was hydrogenated over Raney nickel in ethanolic ammmonia at about 100° C. for about 10 hours. The hydrogenation solution was filtered to remove the catalyst. The filtrate was evaporated to dryness leaving a viscous oil comprising (±)-1-benzoyl-4-amino-6-methoxy-1,2,2a, 3,4,5-hexahydrobenz[c,d]indole formed in the above hydrogenation. The product was a mixture of two racemates named as the cis-(±) and trans-(±)-racemate for convenience. (Optical centers are at C-2a and C-4.) The viscous oil was dissolved in 25 ml. of 1N aqueous hydrochloric acid and the acidic solution washed several times with methylene dichloride. These washings were discarded. The aqueous solution was then made basic (pH=about 12) with aqueous sodium hydroxide and then extracted with chloroform. The chloroform layer was filtered to remove an insoluble material. The chloroform was removed from the filtrate in vacuo. Recrystallization of the resulting residue from a mixture of toluene and hexane yielded 1.48 g. of crystals melting at 140°-144° C. An additional 0.63 g. of a pale yellow glass was obtained from the filtrate; total yield=2.11 g. (90%). It was determined that the crystalline material was one racemic mixture in which the amine group and the ring junction hydrogen were on opposite sides of the hexahydrobenz[c,d]indole ring system, designated as the trans-(±) racemate, and the yellow oil respresented a racemic mixture in which the amine group and the 2a-hydrogen were on the same side of the benz[c,d]indole ring system, designated as the cisracemate. The trans-(±)-racemate, trans-(±)-1-benzoyl-4-amino-6-methoxy-1,2,2a,3,4,5-hexahydrobenz[c,d]indole, had the following elemental analysis:

Analysis Calculated: C, 74.00; H, 6.54; N, 9.08;

Found: C, 74.21; H, 6.57; N, 8.81.

Ultraviolet spectrum: $\lambda_{max}$ (MeOH) 275 nm ($\epsilon$=11,500), 300 nm (sh) ($\epsilon$=9000);

Mass spectrum: 308 (mass peak).

A reaction mixture was prepared from 0.55 g. of the cis-racemate, 0.75 ml. of propionaldehyde and 5 ml. of acetonitrile. Eighteen hundredths grams of sodium cyanoborohydride were added thereto. The pH of the reaction mixture was adjusted to about 7 with a few drops of glacial acetic acid, at which point a vigorous reaction ensued. The reaction mixture was stirred under a nitrogen atmosphere for about three hours with the occasional addition of a drop of glacial acetic acid. At this point in time, TLC indicated there was no longer any peak corresponding to starting material and only one major spot. The solvent was removed from the reaction mixture and the residue treated with 5N aqueous sodium hydroxide. The alkaline layer was extracted with methylene dichloride. The methylene dichloride extracts were combined and the combined extracts dried. Removal of the solvent left a viscous pale yellow oil as a residue. Chromatography of this residual oil over silica gel in an HPLC preparative column using a 1:1 ethyl acetate/toluene solvent mixture as the eluant produced fractions containing cis-(±)-1-benzoyl-4-di-n-propylamino-6-methoxy-1,2,2a,3,4,5-hexahydrobenz[c,d]indole relatively free of contaminating materials according to TLC. Elemental analysis indicated, however, that the product was slightly impure (weight=0.56 g.).

In a later run at twice the scale, the free base obtained in ether solution, as above, was converted to the hydrochloride salt using a slight excess of 2.4 M ethereal HCl; yield=63%. The hydrochloride salt had the following elemental analysis.

Analysis Calculated: C, 69.99; H, 7.75; N, 6.53; Cl, 8.26;

Found: C, 69.92; H, 7.67; N, 6.47; Cl, 8.03.

Ultraviolet spectrum: $\lambda_{max}$ (MeOH) 274 nm ($\epsilon$10 500) 300 nm (sh) ($\epsilon$=7200);

Mass spectrum: 392 (mass peak).

Following the above procedure, 2.41 g. of cis-(±)-1-benzoyl-4-amino-6-methoxy-1,2,2a,3,4,5-hexahydrobenz[c,d]indole in 25 ml. of acetonitrile was reacted with 5.2 ml. of 37% formalin and 0.78 g. of NaBH$_3$CN at pH=7. The reaction mixture was poured into 2N aqueous sodium hydroxide and the alkaline mixture extracted with ether. The ethereal extract was in turn extracted with 1N aqueous hydrochloric acid. The acidic solution was then made basic with 2N aqueous sodium hydroxide and 1-benzoyl-6-methoxy-4-dimethylaminohexahydrobenz[c,d]indole formed in the above reaction, being insoluble in alkali, separated and was extracted into methylene dichloride. Removal of the methylene dichloride yielded a residue which was purified by chromatography over silica gel using ethyl acetate as the eluant. Fractions containing the desired amine base were combined. An excess of 3.2 M ethereal hydrogen chloride was added to the combined fractions and the solvent removed by evaporation to leave 1.99 g. of cis-(±)-1-benzoyl-4-dimethylamino-6-methoxy-1,2,2a, 3,4,5-hexahydrobenz[c,d]indole hydrochloride. The salt had the following physical characteristics:

Ultraviolet spectrum: $\lambda_{max}$ (EtOH) 274 nm ($\epsilon$=12 200) 300 nm (sh) ($\epsilon$=9300);

Mass spectrum: 335 (M-1 peak).

Analysis Calculated: C, 67.64; H, 6.76; N 7.51;

Found: C, 67.77; H, 6.87; N, 7.51.

The above procedure was repeated with the crystalline fraction comprising trans-(±)-1-benzoyl-4-amino-6-methoxy 1,2,2a,3,4,5-hexahydrobenz[c,d]indole. One and sixty-three hundredths grams of this racemate were dissolved in 12.5 ml. of acetonitrile and 1.85 ml. of propionaldehyde were added. Forty-five hundredths grams of sodium cyanoborohydride were then added followed by the dropwise addition of sufficient acetic acid to bring the pH to about 7. The reaction mixture was stirred for about three hours while occasionally adding a drop of glacial acetic acid. At the end of this time, TLC indicated absence of starting material The reaction mixture was therefore poured into 2N aqueous sodium hydroxide solution and the alkaline mixture extracted with ether. The ether extracts were combined and the combined extracts washed with water. The ether solution was then contacted with 1N aqueous hydrochloric acid thereby extracting trans-(±)-1-benzoyl-4-(di-n-propyl)amino-6-methoxy-1,2,2a,3,4,5-hexahydrobenz[c,d]indole formed in the above reaction. The acidic aqueous layer was extracted with ether and the ether extract discarded. The acidic aqueous layer was then made basic with sodium hydroxide and the free base extracted into methylene dichloride. Methylene dichloride was removed by evaporation and the free base remaining was dissolved in dilute aqueous hydrochloric acid containing some methanol The procedure of taking the free base into acidic solution, extracting the acidic solution with ether, making the acidic solution alkaline and reextracting the free base into methylene dichloride was repeated. Evaporation of ethylene dichloride from the final base extract yielded a viscous oil weighing 1.07 g. (63% yield). TLC indicated essentially single spot material. The compound was converted to the hydrochloride salt by standard procedures. Trans-($\pm$)-1-benzoyl-4-di-n-propylamino-6-methoxy-1,2,2a,3,4,5-hexahydrobenz[c,d]indole hydrochloride thus prepared had the following analysis.

Analysis Calculated: C, 69.99; H, 7.75; N, 6.53; Cl, 8.26;

Found: C, 69.92; H, 7.52; N, 6.26; Cl, 8.02.

Ultraviolet spectrum: $\lambda_{max}$ (MeOH) 274 nm ($\epsilon$=10,800), 300 nm (sh) ($\epsilon$=8400);

Mass spectrum: 392 (mass peak).

Trans-($\pm$)-1-benzoyl-4-dimethylamino-6-methoxy-1,2,2a,3,4,5-hexahydrobenz[c,d]indole can be prepared in similar fashion by reductive alkylation of the 6-amino derivative with HCHO and NaBH$_3$CN.

Cis-($\pm$)-1-benzoyl-4-di-n-propylamino-6-methoxy-1,2,2a,3,4,5-hexahydrobenz[c,d]indole (0.507 g.) and 5 ml. of 6N aqueous hydrochloric acid were refluxed under a nitrogen atmosphere for three hours. TLC at the end of this time indicated that hydrolysis of the benzamide group was complete. The aqueous solution was therefore diluted with water. Benzoic acid formed in the hydrolysis crystallized on cooling and was separated by filtration. The acidic aqueous layer was extracted twice with equal volumes of ether to remove the last traces of benzoic acid. The ether extracts were discarded. The acidic aqueous layer was then made basic by addition of 5N aqueous sodium hydroxide. The alkaline layer was extracted several times with methylene dichloride. The methylene dichloride extracts were combined and dried. Evaporation of the methylene dichloride yielded an oil that was purified by passage over a short silica gel column using ethyl acetate as the eluant. The purified product was crystallized from isooctane. Cis-($\pm$)-4-di-n-propylamino-6-methoxy-1,2,2a,3,4,5-hexahydrobenz[c,d]indole thus prepared melted at 75°-78° C. The compound had the following physical characteristics.

Ultraviolet spectrum: $\lambda_{max}$ (EtOH) 237 nm ($\epsilon$=7400), 299 nm ($\epsilon$=3000);

NMR (CDCl$_3$) $\delta$=0.87 (t, 6H, C-CH$_3$), 1.45 (mult, 5H, CH$_2$Me and 3$\beta$—H), 2.20 (sextet, 1H, 3$\alpha$—H) 2.49 (mult 5H CH$_2$Et and 5$\beta$—H), 2.91 (qt, 1H, 5$\alpha$—H), 3.12 (mult, 2H, 2$\beta$—H and 4—H), 3.26 (mult, 1H, 2a—H), 3.64 (t, 1H, 2$\alpha$—H), 3.77 (s, 3H, OCH$_3$), 6.48 (qt, 2H, 7—H and 8—H).

Analysis Calculated: C, 74.96; H, 9.79; N, 9.71;

Found: C, 75.24; H, 9.55; N, 9.60.

Following the above procedure 1.90 g. of cis-($\pm$)-1-benzoyl-4-dimethylamino-6-methoxy-1,2,2a,3,4,5-hexahydrobenz[c,d]indole was debenzoylated by treatment of the hydrochloride salt with acid (20 ml. of 3 M aqueous sulfuric acid). After cooling, the reaction mixture was extracted twice with ether to remove benzoic acid formed as a by-product in the above reaction. The reaction mixture was then made basic with 5 M aqueous sodium hydroxide. Cis-($\pm$)-4-dimethylamino-6-methoxy-1,2,2a,3,4,5-hexahydrobenz[c,d]indole formed in the above reaction separated and was extracted into methylene dichloride. Removal of the solvent from the extract left a dark oil which was purified by chromatography over silica gel using 1:19 methanol-ethyl acetate solvent mixture as the eluant. Removal of the solvent from fractions containing the desired compound yielded 1.06 g. of cis-($\pm$)-4-dimethylamino-6-methoxy-1,2,2a,3,4,5-hexahydrobenz[c,d]indole having the following elemental analysis.

Analysis Calculated: C, 72.38; H, 8.68; N, 12.06;

Found: C, 72.18; H, 8.72; N, 11.83.

The compound had the following physical characteristics:

Infrared spectrum: $\lambda_{max}$ (EtOH) 239 nm ($\epsilon$=7400), 300 nm ($\epsilon$=3100);

Mass spectrum 232 (mass peak).

Trans-($\pm$)-1-benzoyl-4-(di-n-propyl)amino-6-methoxy-1,2,2a,3,4,5-hexahydrobenz[c,d]indole was hydrolyzed in similar fashion to yield (79%) trans-($\pm$)-4-(di-n-propyl)amino-6-methoxy-1,2,2a,3,4,5-hexahydrobenz[c,d]indole melting at 71°-3° C. after recrystallization from isooctane.

The compound had the following physical characteristics:

Infrared spectrum:$\lambda_{max}$ (EtOH) 239 nm ($\epsilon$=7100), 299 nm ($\epsilon$=3100);

NMR (CDCl$_3$) $\delta$=0.89 (t, 6H, C—CH$_3$), 1.41 (quintet, 1H 3$\beta$—H), 1.48 (sextet, 4H, CH$_2$Me), 2.16 (brd, 1H, 3$\alpha$—H), 2.47 (mult, 5H, CH$_2$Et and 5$\beta$—H), 2.83 (qt, 1H, 5$\alpha$—H), 3.14 (mult, 3H, 2a—H and 2$\beta$—H and 4—H), 3.48 (brs 1H N—H), 3.62 (t, 1H, 2$\alpha$—H), 3.77 (s, 3H, OCH$_3$), 6.46 (qt, 2H, 7—H and 8—H).

Analysis Calculated: C, 74.96; H, 9.79; N, 9.71;

Found: C, 74.72; H, 9.57; N, 9.54.

Cis-($\pm$)-4-di-n-propylamino-6-methoxy-1,2,-2a,3,4,5-hexahydrobenz[c,d]indole was oxidized to the tetrahydrobenz[c,d]indole by the following procedure. Three hundred twenty-one thousandths grams of the indoline free base and 0.12 ml. of dimethylsulfide were dissolved in 5 ml. of methylene dichloride. The solution was cooled to about $-70°$ C. in a dry ice-acetone bath. A solution of 0.175 ml. of t-butylhypochlorite in 3 ml. of methylene chloride was added to the reaction mixture over a 30 minute period. After the addition had been completed, the reaction mixture was stirred for two hours at dry ice-acetone temperatures. Next a solution of 0.13 g. of sodium and 3 ml. of ethanol was added, also in dropwise fashion. The resulting mixture was allowed to warm to room temperature and was stirred at that temperature for about one hour, at which time it was washed twice with water and the water wash discarded. The solvent was removed from the organic layer to leave a dark brown residue which was chromatographed over silica gel. The chromatographic column was prepared in a solvent mixture comprising 10% triethylamine, 10% ethyl acetate and 80% toluene. The desired product was eluted with a 1:9 ethyl acetate/toluene solvent mixture. Chromatographic fractions containing this product were combined and the solvent removed therefrom in vacuo leaving a colored residual free base consisting of ($\pm$)-4-di-n-propylamino-6-methoxy-1,3,4,5-tetrahydrobenz[c,d]indole formed in the above oxidation. The residual oil was converted to the hydrochloride salt which decomposed at about 110° C. The salt had the following analysis:

Analysis Calculated: C, 66.96; H, 8.43; N, 8.68; Cl, 10.98;

Found: C, 66.84; H, 8.58; N, 8.44; Cl, 10.76.

NMR (CDCl$_3$) $\delta$=1.02 (mult, 6H, 2—CH$_3$), 1.99 (mult, 4H, CH$_2$Me), 2.94 (mult, 1H, 5$\beta$—H), 3.04 (qt, 1H, 5$\alpha$—H), 3.17 (mult, 5H, CH$_2$Et and 3$\alpha$—H), 3.47 (mult, 1H, 3$\beta$—H), 3.80 (t, 1H, 4—H), 3.89 (s, 3H, OCH₃), 6.85 (d, 1H, 8—H), 6.94 (s, 1H, 2—H), 7.19 (d, 1H, 7—H), 8.18 (s, 1H, N—H), 12.14 (brs, 1H, HCl);

Mass spectrum: 286 (mass peak).

The trans-(±)-racemate was oxidized in a slightly different fashion as follows. A solution of 0.35 g. of 98% N-chlorosuccinimide in 10 ml. of distilled methylene dichloride was cooled to about 0° C. while 0.3 ml. of methylsulfide were added in dropwise fashion under a nitrogen atmosphere. After stirring at ice bath temperature for 15 minutes, the solution was cooled to dry ice-acetone temperature (−70° C.). Next, a solution of 0.72 g. of trans-(±)-4-di-n-propylamino-6-methoxy-1,-2,2a,3,4,5-hexahydrobenz[c,d]indole in 2 ml. of methylene dichloride was added in a dropwise fashion over a 30 minute period. The resulting reaction mixture was stirred for another 30 minutes after which time 1 ml. of triethylamine was added in dropwise fashion. This new reaction mixture was stirred at dry ice-acetone temperature for another 15 minutes and was then allowed to warm to room temperature. The reaction mixture was next washed three times with water and the water extracts reextracted with ether. The methylene dichloride solution and ether extracts were combined and the solvent removed therefrom in vacuo leaving a viscous brown oil. Chromatography over silica gel (as with the cis-racemate) gave 0.303 g. of (±)-4-di-n-propylamino-6-methoxy-1,3,4,5-tetrahydrobenz[c,d]indole formed in the above reaction. Two hundred thirty-five hundredths grams of free base were eventually obtained and converted to the hydrochloride salt using ethereal hydrogen chloride (2.38 molar).

Following the above procedure, a solution of 0.78 g. of N-chlorosuccinimide and 0.5 ml. of dimethylsulfide in 25 ml. of toluene was used to oxidize 1.0 g. of cis-(±)-4-dimethylamino-6-methoxy-1,2,2a,3,4,5-hexahydrobenz[c,d]indole at dry ice-acetone temperatures. One and twenty-five hundredths ml. of triethylamine were added. The reaction mixture was worked up and the crude residue, comprising (±)-4-dimethylamino-6-methoxy-1,3,4,5-tetrahydrobenz[c,d]indole formed in the above oxidation, was purified by chromatography over silica gel. Ethyl acetate containing increasing (0–5%) methanol was used as the eluant. Fractions containing the desired tetrahydrobenz[c,d]indole were combined to yield 0.15 g. of the compound The free base in ethereal solution was converted to the hydrochloride salt with 4.5 M ethereal HCl, which salt had the following elemental analysis.

Analysis Calculated: C 63.03; H, 7.18; N, 10.50; Cl, 13.29;
Found C, 62.83; H, 7.10; N, 10.29; Cl, 13.14.

The compound had the following physical characteristics:

NMR (CDCl₃) δ=2.86 (d, 3H, NCH₃), 2.9 (mult 1H, 5β—H), 2.97 (d, 3H, NCH₃), 3.04 (qt, 1H, 5α—H) 3.18 (qt, 1H, 3α—H), 3.51 (qt, 1H, 3β—H), 3.71 (mult, 1H, 4—H), 3.90 (s, 3H, OCH₃), 6.87 (d, 1H, 8—H), 6.96 (s, 1H, 2—H), 7.19 (d, 1H, 7—H), 8.00 (s, 1H, N—H), 12.79 (brs, H, HCl);

Mass spectrum: 230 (mass peak).

EXAMPLE 2

Alternative Preparation of (±)-4-di-n-propylamino-6-methoxy-1,3,4,5-tetrahydrobenz[c,d]indole A mixture containing 5.0 g. of 5-oxo-1,2,2a,3,-4,5-hexahydrobenz[c,d]indole in 100 ml. of ethanol was treated with 1.63 g. of sodium borohydride in portions. The resulting mixture was stirred for about four hours after which time the bulk of the ethanol was removed in vacuo. The resulting residue was taken up in water, and the aqueous mixture acidified with 3M hydrochloric acid. The aqueous solution was filtered, and the filtrate treated with dilute aqueous sodium hydroxide. (±)-5-Hydroxy-1,2,2a,3,4,5,-benz[c,d]indole formed in the above reaction was insoluble in the basic medium and precipitated. The precipitate was collected, washed with water and then dried. Four and seventy-two hundredths grams of (±)-5-hydroxy-1,2,2a,3,4,5-hexahydrobenz[c,d]indole (93% yield) were obtained. The material was one spot by TLC; m.p.=205° C.

Analysis Calculated: C, 75.83; H, 6.94; N, 8.04;
Found: C, 75.75; H, 7.16; N, 7.89.

A solution of 35 of (±)-5-hydroxy-1,2,2a,-3,4,5-hexahydrobenz[c,d]indole in 900 ml. of cold glacial acetic acid was treated with 22 g. of bromine dissolved in 100 ml. of glacial acetic acid. After the bromine color had been discharged, the acetic acid was removed in vacuo. The residue, comprising a mixture of (±)-5-hydroxy-6-bromo-1,2,2a,3,4,5-hexahydrobenz[c,d]indole and the corresponding 6,8-dibromo derivative was diluted with water and the aqueous mixture made basic with 5M aqueous sodium hydroxide. The hexahydrobenz[c,d]indoles, being insoluble in base, precipitated, and the precipitate was collected. Recrystallization of the precipitate from methanol yielded about 3 g. of the dibromo derivative plus about 12.5 g. of the monobromo derivative and a considerable quantity of a crystal fraction which was a 1:1 mixture of starting material and monobromo derivative. (±)-5-Hydroxy-6-bromo-1,2,2a,3,4,5-hexahydrobenz[c,d]indole thus formed melted at about 172° C. with decomposition. Twenty-four and one tenth grams (47% yield) of the 6-bromo derivative were obtained by recrystallization of various fractions. The product as obtained still contained a small amount of the dibromo impurity.

A reaction mixture was prepared by dissolving 27.43 g. of (±)-5-hydroxy-6-bromo-1,2,2a,3,4,5-hexahydrobenz[c,d]indole in 100 ml. of pyridine and then adding in dropwise fashion 25 ml. of ethyl chloroformate over a 20 minute period. About 0.5 g. of 4-(N,N-dimethylamino)pyridine (DMAP) were added, and the resulting reaction mixture stirred at room temperature for about four hours. The reaction mixture was then quenched by pouring into 1 liter of an ice-water mixture. An oil which separated crystallized almost immediately. The crystals were collected and washed thoroughly with water. The dried ester amide was a faintly pink solid melting above 215° C. with decomposition; yield=40.48 g. (94%). Analysis indicated that some 6,8-dibromo compound continued as a contaminate.

Forty and one tenth grams of (±)-1-ethoxycarbonyl-5-ethoxycarbonyloxy-6-bromo-1,2,2a,3,4,5-hexahydrobenz[c,d]indole were pyrolized in four different ten gram runs at 215°-220° C. under a nitrogen atmosphere. Each run required 25-30 minutes of heating. The four dark oily residues were combined, and the combined residues taken up in toluene. The toluene solution was chromatographed over silica. One and four tenths grams of starting material were recovered from fractions containing it but the main product—1-ethoxycarbonyl-6-bromo-1,2,2a,3-tetrahydrobenz[c,d]indole—was recrystallized from a hexane/toluene solvent mixture containing predominantly hexane to yield 19.36 g including a second crop, from hexane alone. Yield=65% corrected for recovered starting material. The compound melted at 122°–123° C.

Analysis Calculated: C, 54.56; H, 4.58; N, 4.55; Br, 25.93;
Found: C, 54.59; H, 4.61; N, 4.41; Br, 25.84.

The unsaturated product from the above step was epoxidized as follows:

A solution of 7.5 g. of 1-ethoxycarbonyl-6-bromo-1,2,2a,3-tetrahydrobenz[c,d]indole in 250 ml. of chloroform was cooled to about 0° C. with an ice/salt mixture. Six grams of 85% of m-chloroperbenzoic acid were added. The reaction mixture was stirred at about 0° C. for one hour and was then kept at refrigerator temperature overnight. The reaction mixture was washed successively with 1N aqueous sodium hydroxide, saturated aqueous sodium bisulfite, again with 1N aqueous sodium hydroxide and finally with brine. The organic solution was dried, and the solvent removed in vacuo. The resulting solid residue was recrystallized from a toluene/hexane solvent mixture. The first crop material obtained weighed 7.33 g. and melted at 126°–8° C.; total yield (2 crops)=98%.

Analysis Calculated: C, 51.87; H, 4.35; N, 4.32; Br, 24.65;
Found: C, 51.83; H, 11.33; N, 4.16; Br, 24.31.

A solution of 7.5 g. of 1-ethoxycarbonyl-4,5-epoxy-6-bromo-1,2,2a,3,4,5-hexahydrobenz[c,d]indole obtained as above in 50 ml. of benzene was added slowly to a refluxing solution of 1 g. of zinc iodide in 450 ml. of benzene which had been dried by distilling off 50 ml. of the benzene-water azeotrope. Reflux under a nitrogen atmosphere was continued for one hour after the addition had been completed. The reaction mixture was cooled The supernate was decanted, and the decanted solution washed with water and then with brine. The solution was dried and the solvent removed therefrom in vacuo. The residue, comprising 1-ethoxycarbonyl-4-oxo-6-bromo-1,2,2a,3,4,5-hexahydrobenz[c,d]indole formed in the above reaction, was crystallized from a toluene/hexane solvent mixture. Five and thirty-six hundredths grams (71% yield) of crystalline product melting at 186°–8° C. were obtained.

Analysis Calculated: C, 51.87; H, 4.35; N, 4.32; Br, 24.65;
Found: C, 51.75; H, 4.29; N, 4.50; Br, 24.80.

A reaction mixture was prepared from 14 g. of 1-ethoxycarbonyl-4-oxo-6-bromo-1,2,2a,3,4,5-hexahydrobenz[c,d]indole, 28.3 g. of n-propylamine, 4.9 ml. of glacial acetic acid and 300 ml. of acetonitrile. The reaction mixture was stirred under a nitrogen atmosphere for about one hour. 3Å molecular sieves were added to absorb water. Next, 5.6 g. of sodium cyanoborohydride were added followed by 14 ml. of glacial acetic acid. This new reaction mixture was stirred for an additional two hours at which time 7 ml. of glacial acetic acid were added. The reaction mixture was stirred for another two hours, and another 7 ml. of glacial acetic acid added. Finally, the supernate was decanted from the molecular sieves, and the bulk of the volatile constituents were removed in vacuo. The residual solution was poured into cold 2N aqueous sodium hdyroxide. The alkaline mixture was extracted with methylene dichloride. The methylene dichloride extract was washed with 0.5N aqueous sodium hydroxide and then with brine. The solvent was removed in vacuo. The resulting residue was dissolved in 1N aqueous hydrochloric acid to which methanol had been added. This acidic solution was washed with ether, and the ether wash discarded. The acidic solution was then made basic with 5N aqueous sodium hydroxide, and the now insoluble (±)-1-ethoxycarbonyl-4-n-propylamino-6-bromo-1,2,2a, 3,4,5-hexahydrobenz[c,d]indole formed in the above reaction separated and was extracted into methylene dichloride. The methylene dichloride extract was separated, and the solvent removed therefrom to yield 16.7 g. of an orange oil which was used in the next step without further purification.

The above crude product was dissolved in 50 ml. of acetonitrile, 3 ml. of n-propyl iodide and 2 ml. of diisopropylethylamine. This solution was allowed to remain in the dark for about three weeks. At this point in time, the solvent was removed under reduced pressure, and the residual mixture partitioned between ether and 0.5N aqueous sodium hydroxide. The organic layer was separated, and the aqueous alkaline layer extracted several times more with ether. The ether extracts were combined and the combined extracts washed with brine and then dried. The ether was removed in vacuo to yield a residue. Xylene was added to the residue and removed by evaporation to remove any remaining diisopropylethylamine. The unpurified residue slowly crystallized. The crystals were dissolved in 20 ml. of methylene dichloride and 1 ml. of acetic anhydride was added thereto. After about an hour, the volatile constituents were removed in vacuo and the resulting residue dissolved in methylene dichloride. The methylene dichloride solution was stirred with aqueous saturated sodium carbonate to remove any excess acetic anhydride. The methylene dichloride layer was separated, and the methylene dichloride removed by evaporation. The residue was dissolved in a mixture of dilute hydrochloric acid and methanol. The resulting cloudy solution was washed with ether and the ether was discarded. The acidic layer was then made basic with 5N aqueous sodium hydroxide and the now insoluble base which separated was extracted into methylene dichloride. Evaporation of the solvent gave a moist crystalline residue. The residue was treated with hexane, and the hexane solution separated from hexane-insoluble brown oil by decantation. The hexane was evaporated in vacuo, and the residue chromatographed over 25 g. of silica gel using ethyl acetate as the eluant. Fractions containing the desired material were combined and the solvent removed therefrom in vacuo. The white, crystalline residue was transferred to a filter paper using cold isooctane. A total yield of 2.39 g. of (±)-1-ethoxycarbonyl-4-di-n-propylamino-6-bromo-1,2,2a,3,4,5-hexahydrobenz[c,d]indole was obtained in two crops. m.p.=90°–94° C.

Analysis Calculated: C, 58.68; H, 7.14; N, 6.84; Br, 19.52;
Found: C, 58.98; H, 6.88; N, 6.59; Br, 19.74.

Alternatively, a solution of 15.7 g. of the crude secondary amine. (±)-1-ethoxycarbonyl-4-n-propylamino-6-bromo-1,2,2a,3,4,5-hexahydrobenz[c,d]indole in 80 ml. of pyridine was cooled to about 0° C. Sixteen ml. of propionic anhydride were added slowly. The solution was allowed to remain at ambient temperature overnight. The bulk of the pyridine solvent was removed under vacuum, and the residual solution was stirred with an excess of aqueous sodium carbonate for several hours to remove any unreacted propionic anhydride and any by-product propionic acid. The aqueous mixture was extracted with methylene dichloride, and the methylene dichloride extract separated and washed with 0.5M aqueous sodium hydroxide, 1N hydrochloric acid and brine. The organic solution was dried and the solvent removed therefrom in vacuo leaving a viscous oil. The oil was dissolved in 50 ml. of THF and this solution added over about a 15 minute period to 85 ml. of 1M diborane in THF kept at about 0° C. After the addition had been completed, the cooling bath was removed, and the reaction mixture heated to reflux temperature for about 1.5 hours. The reaction mixture was then cooled to about 0° C. and 50 ml. of methanol were added cautiously. The resulting reaction was stirred over-night at room temperature. The methanol was removed in vacuo. Additional methanol was added and again removed by evaporation. The resulting residue began to solidify. The semisolid residue was partitioned between diethyl ether and 1M hydrochloric acid containing added methanol. The solid which precipitated as a result of these operations was collected by filtration. The filtrate was made basic by the addition of aqueous sodium hydroxide, and the alkaline mixture extracted with methylene dichloride. The above ether layer, the methylene dichloride extract and the separated solid were combined and the solvent evaporated. The residue was heated with wet DMSO, and this solution was then diluted with water plus sufficient 1M aqueous sodium hydroxide to maintain basic conditions. The alkaline mixture was extracted with ether. The ether extract was in turn extracted with 1M hydrochloric acid containing some methanol. The acidic extract was again made basic, and the resulting alkaline mixture extracted with methylene dichloride. The methylene dichloride extracts were combined. Upon evaporation of the solvent, fifteen and fifty-nine hundredths grams of crude salmon colored compound were obtained. The solid was dissolved in ethyl acetate and chromatographed over silica gel. Fractions containing the desired material were combined and the solvent removed therefrom in vacuo. Recrystallization of the resulting solid from isooctane gave (±)-1-ethoxycarbonyl-4-di-n-propylamino-6-bromo-1,2,2a,3,4,5-hexahydrobenz[c,d]indole melting 87°-9° C.; yield=14.8 g. (94%).

A solution of 1 g. of the above tertiary amine in 10 ml. of 6N hydrochloric acid was heated to reflux temperature under nitrogen overnight. TLC indicated that only a trace of starting material remained and that the chief product was (±)-4-di-n-propylamine-6-bromo-1,2,2a,3,4,5-hexahydrobenz[c,d]indole. The acidic solution was poured into dilute aqueous sodium hydroxide, and the resulting alkaline layer extracted with methylene dichloride. The methylene dichloride extract was separated and the separated extract washed with brine and then dried. Evaporation of the solvent yielded a viscous oil which crystallized upon cooling. Recrystallization of the precipitate from isooctane gave 0.683 g. 83% yield) of (±)-4-di-n-propylamino-6-bromo-1,2,2a,3,4,5-hexahydrobenz[c,d]indole melting at about 62°-3° C.

Analysis Calculated C, 60.53; H, 7.47; N, 8.31; Br, 23.69;
Found: C, 60.71; H, 7.57; N, 8.30; Br, 23.78.

A run on a larger scale (14.8 g. of starting material) gave an 88% yield of the desired hydrolysis product.

A suspension of 0.44 g. of N-chlorosuccinimide in 16 ml. of toluene was chilled to about 0° C. Three tenths ml. of dimethylsulfide were added. After 15 minutes, the reaction mixture was cooled in a dry iceacetone bath to about −60° C. Six tenths grams of (±)-4-di-n-propylamino-6-bromo-1,2,2a,3,4,5-hexahydrobenz[c,-d]indole (prepared in Example A) and 2 ml. of toluene were added over a 15 minute period. The reaction mixture was stirred at about −60° C for about two hours at which point 0.8 ml. of triethylamine were added. The cooling bath was removed and stirring continued for about 2½ hours at ambient temperature. The reaction mixture was then poured into cold 1N aqueous sodium hydroxide and the now alkaline mixture extracted several times with toluene. The toluene extracts were combined, and the combined extracts washed with brine and then dried. The solvent was removed and the resulting residue chromatographed over 15 g. of Florosil using a 1:9 ethyl acetate/toluene solvent mixture as the eluant. Fractions containing the desired product were combined and rechromatographed over silica using the same eluant. Fractions containing the desired product were again combined and the solvent evaporated therefrom to leave a slightly greenish oil. This oil was dissolved in about 20 ml. of pentane and filtered to remove a colorless precipitate. The pentane was then removed by evaporation in vacuo. A yellow green oil weighing 0.303 g. (51% yield) was obtained comprising (±)-4-di-n-propylamino-6-bromo-1,3,4,5-tetrahydrobenz[c,d]indole formed in the above oxidation. The product crystallized upon standing; m.p.=72°-3° C.

Analysis Calculated: C, 60.90; H, 6.91; N, 8.36; Br, 23.83;
Found: C, 60.77; H, 6.87; N, 8.28; Br, 23.61.

Alternatively, a solution of 1 g. of (±)-4-di-n-propylamino-6-bromo-1,2,2a,3,4,5-hexahydrobenz[c,-d]indole and 50 ml. of hexane was prepared. Four grams of activated manganese dioxide were added and the resulting suspension sonicated (50–55 KHz) under a nitrogen atmosphere for about one hour. TLC at this point indicated almost no starting material remaining. The reaction mixture was suction filtered, and the precipitate of magnese dioxide obtained was thoroughly washed with fresh hexane. The hexane was removed from the filtrate and the resulting residue chromatographed as before. Fractions containing the desired indole were combined and the solvent removed by evaporation. Recrystallization of the resulting residue from isooctane yielded 0.62 g. 62% yield) of (±)-4-di-n-propylamino-6-bromo-1,3,4,5-tetrahydrobenz[c,d]indole melting at 73°-4° C.

A solution of sodium methylate was prepared by dissolving 0.276 g. of sodium metal in 3 ml. of methanol. Ten ml. of DMF were addded followed by 0.3 g. of CuI. 0.20 g. of (±)-4-di-n-propylamino-6-bromo-1,3,4,5-tetrahydrobenz[c,d]indole were added to the resulting suspension. The reaction mixture was heated at about 130° C. under N for about 5 hours. The reaction mixture was filtered, and the filter cake washed thoroughly with DMF. Cold water was added to the filtrate. The aqueous layer was extracted three times with ether. The combined ether extracts were washed with brine and dried. Removal of the ether in vacuo left a residue which was chromatographed over SiO$_2$ using 1:1 ethyl acetate/toluene as the eluant. Late fractions containing the desired 6-methoxy derivative were combined and the solvent removed in vacuo. The viscous oily product was seeded with previously obtained crystals of the 6-methoxy derivative. Recrystallization from isooctane yielded (±)-4-di-n-propylamino-6-methoxy-1,3,4,5-tetrahydrobenz[c,d]indole melting at 87°–9° C.; yield=80%.

Analysis Calculated: C, 75.48 H, 9.15; N, 9.78;
Found: C, 75.64; H, 9.25; N, 9.62.

The central serotonergic action of drugs according to IV above was demonstrated in two ways. The first method was to show inhibition of tritiated serotonin uptake according to the following protocol. (Weak inhibition of tritiated spiperone uptake was also determined.) Several (±)-4-di-n-propylamino-6-substituted-1,3,4,5-tetrahydroindoles plus the corresponding drug from Bach-Kornfeld U.S. Pat. No. 4,110,339 lacking a C-6 substituent were tested.

Brain tissue was obtained from 150–200 g. male Wistar rats. The cerebral cortex was dissected out and then homogenized and centrifuged according to the method described by Nelson and coworkers Mol. Pharmacol., 14, 983–995 (1978), using preincubation in buffer without added monoamine oxidase inhibitor in order to eliminate endogenous serotonin. For receptor binding, each sample contained 300–400 μg. of membrane protein and 10 μM pargyline in addition to the $^3$H-ligand in 1 ml. of 0.05 M Tris buffer, pH=7.4. The assay of serotonin binding was done following the method of Bennett and Snyder, Mol. Pharmacol., 12, 373–389 (1976), and that for tritiated spiperone according to Peroutka and Snyder, Mol. Pharmacol. 16 687–699 (1979). The samples were incubated for 15 minutes at 37° and were then filtered through GF/C glass fiber filter pads using a Brandel M-24 cell harvester modified for receptor binding. After two 5 ml. rinses, the filter discs were put into scintillation vials and counted in 10 ml. of Amersham PCS scintillation fluid. Nonspecific binding of $^3$H-serotonin ($^3$H-5HT) was determined in the presence of $10^{-5}$M serotonin and of $^3$H-spiperone in the presence of $10^{-6}$M LSD. Specific binding was calculated as the difference between total binding with no added nonradioactive compound and the nonspecific binding. IC$_{50}$ values were determined where the IC$_{50}$ is the amount of substance causing 50 percent inhibition of the specific binding using 10–12 concentrations in the range of $10^{-9}$ to $10^{-4}$M. The concentrations of $^3$H-ligands were: serotonin (Amersham, 11 Ci/mmol), 2–3 nM; LSD (Amersham, 1.8 Ci/mmol), 1.8–2.6 nM; spiperone (Amersham, 20 Ci/mmol), 0.6–0.7 nM.

The results obtained, are set forth in Table 1.

TABLE 1

| | RECEPTOR BINDING | |
| --- | --- | --- |
| | $^3$H-Ligand-IC$_{50}$* | |
| Name of Compound | $^3$H-5HT | $^3$H-SPIP |
| (±)-4-dimethylamino-6-methoxy-1,3,4,5-tetrahydrobenz[c,d]indole | 70 | 1490 |
| (±)-4-di-n-propylamino-6- | 50 | 950 |

TABLE 1-continued

| | RECEPTOR BINDING | |
| --- | --- | --- |
| | $^3$H-Ligand-IC$_{50}$* | |
| Name of Compound | $^3$H-5HT | $^3$H-SPIP |
| methoxy-1,3,4,5-tetrahydrobenz[c,d]indole | | |
| (±)-4-dimethylamino-1,3,4,5-tetrahydrobenz-[c,d]indole | 120 | 730 |

*Values are in nanomoles of inhibitor.

Secondly, as a measure of central serotonin agonist activity, the decrease of serotonin metabolites in brain was measured. Also the measure of dopamine agonist activity was indicated by changes in dopamine metabolites.

The following protocol was employed. 150–200 g. Wistar rats were given 0.3 mg/kg subcutaneously of (±)-4-di-n-propylamino-6-substituted-1,3,4,5-tetrahydrobenz[c,d]indole. Then, 60 minutes later each rat was decapitated and the hypothalamus and striatum were dissected out and extracted. The amounts of homovanillic acid (HVA) and 3,4-dihydroxyphenylacetic acid (DOPAC) in the striatum and of 5-hydroxyindoleacetic acid (5HIAA) in the hypothalamus were measured by high-performance liquid chromatography, using electrochemical detection. Serum corticosteroids were also measured. Table 2 gives the results of this experiment. In the table, columns 1 and 2 give the substitution pattern in the compounds of formula IV, columns 3–5, the 5HT or dopamine metabolite concentrations, and column 6, the serum corticosteroids.

TABLE 2

| X | R$^1$ and R$^2$ | 5HIAA In Hypothalamus NMoles/G | Dopamine Metabolites In Striatum, NMoles/G | | Serum Corticosterone MCG/100 ML |
| --- | --- | --- | --- | --- | --- |
| | | | DOPAC | HVA | |
| OMe | di-nPr | 1.51 ± .05* | 4.61 ± .10* | 2.43 ± .18* | 48 ± 2* |
| OMe | di-Me | 1.69 ± .07* | 7.15 ± .23* | 4.68 ± .21 | 41 ± 4* |
| | (control) | 2.59 ± .11 | 5.58 ± .38 | 4.24 ± .27 | 7 ± 1 |

Compounds were injected at 0.3 mg/kg s.c. 1 hour before rats were killed.
*statistically significant Thirdly, as a measure of central serotonin agonist activity, the test rats received (±)-4-di-n-propylamino-6-methoxy-1,3,4,5-tetrahydrobenz[c,d]indole. The decrease of serotonin turnover in brain was measured as a function of 5-hydroxytryptophane (5-HTP) accumulation when the decarboxylation of 5-HTP is blocked by m-hydroxybenzylhydrazine, using the above protocol, except that thirty minutes after injection of the drug, m-hydroxybenzylhydrazine was injected at 100 mg./kg. i.p. Then, 40 minutes later each rat was decapitated, the hypothalamus dissected out and extracted. The amount of 5-HTP in each extract were measured by high-performance liquid chromatography, using electrochemical detection. In normal rats, 5-HTP brain levels are so low as to be virtually undetectable. Thus, the control group received the same dose of m-hydroxybenzylhydrazine as the test rats but no drug. Table 3 gives the results of this experiment.

TABLE 3

| UPTAKE INHIBITION | |
| --- | --- |
| Dose of Drug Mg./Kg. | 5HTP Level in Nanomoles of Hypothalamus ± S.E. |
| 0 | 1.81 ± 0.11 |
| 0.01 | 1.85 ± 0.06 |
| 0.03 | 1.72 ± 0.07 |

TABLE 3-continued

| UPTAKE INHIBITION | |
|---|---|
| Dose of Drug Mg./Kg. | 5HTP Level in Nanomoles of Hypothalamus ± S.E. |
| 0.10 | 1.16 ± 0.05* |
| 0.30 | 0.97 ± 0.03* |

*Significant difference from zero dose group (P < .05).

The above results indicate that certain dose levels of (±)-4-di-n-propylamino-6-methoxy-1,3,4,5-tetrahydrobenz[c,d]indole significantly decreased 5HTP accumulation, thus indicating central serotonin agonist activity at those dosage levels or at higher dosage levels.

Drugs which have central serotonin agonist activity are useful as antidepressants. The compounds of formula IV which have such central serotonergic activity to a marked degree with minimal agonist or antagonist actions toward NE or dopamine should be particularly useful in that their use would not be accompanied by side effects common to presently marketed antidepressants, particularly the antimuscarinic effect. Several of the marketed antidepressants are also monamine oxidase inhibitors, a nonspecific amine oxidase linked with metabolic degradation of both catecholamines and serotonin, which activity is also lacking in the drugs of formula IV.

The novel drugs of formula IV can be administered parenterally as an isotonic solution of a pharmaceutically acceptable salt. Preferably, however, the drugs are administered orally. For such route of administration, the drug is mixed with one or more pharmaceutical excipients and loaded into empty telescoping gelatin capsules or compressed into tablets, each tablet or capsule to contain a unit antidepressant dosage of the drug.

I claim:

1. A 4-substitutedamino-6-substituted-1,3,4,5-tetrahydrobenz[c,d]indoles of the formula

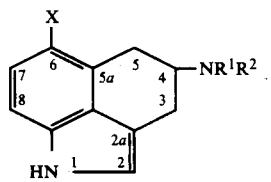

wherein $R^1$ and $R^2$ are individually hydrogen, methyl, ethyl, n-propyl or allyl, and X is $OC_{1-3}$ alkyl, O-benzyl, or O-acyl or OH; wherein acyl is a member of the group benzoyl, naphthoyl, mono-or di-substituted benzenesulfonyl where said substituents are members of the group methyl, halo or $C_{1-2}$ alkoxy, $C_{1-3}$ alkyl CO, $C_{1-3}$ alkyl $SO_2$, $C_{3-7}$ cycloalkylcarbonyl, cyclobutylsulfonyl, methylenedioxybenzoyl or anisoyl; and pharmaceutically acceptable salts thereof.

2. A compound according to claim 1 in which X is $OC_{1-3}$ alkyl.

3. A compound according to claim 2 in which X is $OCH_3$.

4. A compound according to claim 1 in which X is OH or O-acyl wherein acyl is member of the group benzoyl, naphthoyl, mono- or di-substituted benzenesulfonyl where said substituents are members of the group methyl, halo or $C_{1-2}$ alkoxy, $C_{1-3}$ alkyl CO, $C_{1-3}$ alkyl $SO_2$, $C_{3-7}$ cycloalkylcarbonyl, cyclobutylsulfonyl, methylenedioxybenzoyl or anisoyl.

5. A compound according to claim 1 which $R^1$ and $R^2$ are the same $C_{1-3}$ alkyl group.

6. A compound according to claim 1 in which $R^1$ and $R^2$ are both n-propyl.

7. A compound according to claim 1, said compound being (±)-4-(di-n-propyl)amino-6-methoxy-1,3,4,-5-tetrahydrobenz[c,d]indole.

8. The hydrochloride salt of the compound of claim 1.

9. A pharmaceutical formulation in unit dosage form comprising per unit dosage, an amount of a compound according to claim 1 to alleviate the symptoms of depression plus one or more pharmaceutical excipients.

10. A formulation according to claim 9 in which a pharmaceutically acceptable salt of (±)-4-(di-n-propyl)amino-6-methoxy-1,3,4,5-tetrahydrobenz[c,d]indole is the active drug.

11. A method of treating depression which comprises administering to a depressed individual in need of treatment an antidepressant dose of a compound according to claim 1.

12. A therapeutic process according to claim 11 in which (±)-4-(di-n-propyl)amino-6-methoxy-1,3,4,5-tetrahydrobenz[c,d]indole in the form of a pharmaceutically acceptable salt is administered.

13. A formulation according to claim 9 in which a unit dosage formulation is adapted for oral administration.

14. A therapeutic process according to claim 11 in which the drug is administered by the oral route.

15. Compounds of the formula:

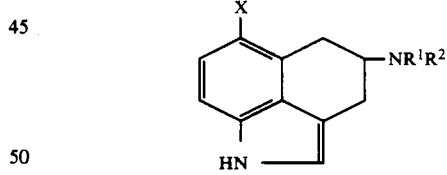

wherein:

X is —OH or —O—lower alkyl;

$R^1$ and $R^2$ are independently H, lower alkyl or lower alkenyl; or a pharmaceutically acceptable salt thereof.

* * * * *